United States Patent [19]

Kruse

[11] 4,024,193
[45] May 17, 1977

[54] HOMOGENEOUS HYDROGENATION PROCESS

[75] Inventor: Walter M. Kruse, Wilmington, Del.

[73] Assignee: ICI United States Inc., Wilmington, Del.

[22] Filed: Nov. 7, 1975

[21] Appl. No.: 629,885

Related U.S. Application Data

[63] Continuation-in-part of Ser. No. 407,871, Oct. 19, 1973, Pat. No. 3,935,284.

[52] U.S. Cl. .............. 260/618 D; 252/431 P; 260/618 H; 260/633; 260/635 A
[51] Int. Cl.² ............... C07C 29/00; C07C 29/14
[58] Field of Search ....... 260/618 H, 638 B, 635 A, 260/621 K, 618 D, 633; 252/431 P

[56] References Cited
UNITED STATES PATENTS

| | | | |
|---|---|---|---|
| 3,110,747 | 11/1963 | Mullineaux | 252/431 P |
| 3,454,644 | 7/1969 | Dewhurst | 260/638 B |
| 3,766,271 | 10/1973 | Knifton | 252/431 P |
| 3,767,709 | 10/1973 | Fenton | 252/431 P |
| 3,793,355 | 2/1974 | Wilkinson et al. | 252/431 P |
| 3,804,868 | 4/1974 | Chabardis et al. | 252/431 P |
| 3,804,869 | 4/1974 | Chabardis et al. | 252/431 P |
| 3,857,900 | 12/1974 | Wilkinson | 260/618 H |
| 3,883,580 | 5/1975 | Solodar et al. | 260/618 H |
| 3,906,045 | 9/1975 | Knifton et al. | 252/431 P |
| 3,933,919 | 1/1976 | Wilkinson | 252/431 P |

Primary Examiner—Norman Morgenstern

[57] ABSTRACT

A homogeneous hydrogenation process is disclosed. The process, which is useful in the preparation of hydrogenated derivatives of compounds having one of the following formulas $RH_2C-CO-CH_2R$

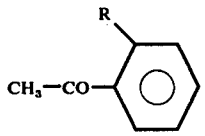

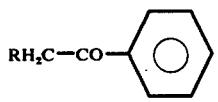

wherein R is —Cl, —Br, —F, or —OH, comprises contacting a solution of one of these compounds with hydrogen in the presence of a catalyst comprising a ruthenium triphenyl phosphine complex and a strong acid.

17 Claims, No Drawings

HOMOGENEOUS HYDROGENATION PROCESS

BACKGROUND OF THE INVENTION

This application is a continuation-in-part of application Ser. No. 407,871 filed Oct. 19, 1973 now U.S. Pat. No. 3,935,284.

FIELD OF THE INVENTION

The present invention relates generally to a homogeneous hydrogenation process. More particularly, the invention relates to a homogeneous hydrogenation process comprising contacting a solution of a compound having one of the following formulas:

$RH_2C-CO-CH_2R$ $CH_3-CO-\underset{R}{\underset{|}{\bigcirc}}$ $RH_2C-CO-\bigcirc$ wherein R is —Cl, —Br, —F or —OH with hydrogen in the presence of a catalyst comprising a ruthenium triphenyl phosphine complex and a strong acid.

DESCRIPTION OF THE PRIOR ART

The hydrogenation of a variety of organic compounds by contacting a solution of the compound with molecular hydrogen in the presence of a hydrogenation catalyst is well known in the art. As is also well known, hydrogenation processes are generally classifiable into one of two broad catagories, depending upon the physical phase in which the catalsyt is present during the hydrogenation process. In the first type, referred to as a heterogeneous hydrogenation process, the catalyst is essentially insoluble in the reaction medium. By comparison, in the second type, referred to as a homogeneous hydrogenation process, the catalyst is essentially completely soluble in the reaction medium.

The use of ruthenium containing materials as catalysts in both heterogeneous and homogeneous hydrogenation processes has also been reported. In U.S. Pat. No. 2,868,847 issued to Boyers, it is disclosed that ruthenium containing catalysts may be utilized in a heterogeneous process for preparing hydrogenated derivatives of mono- and di-saccharides. In U.S. Pat. No. 3,454,644 isssued to Dewhirst, a homogeneous hydrogenation process is disclosed utilizing a ruthenium or osmium metal complex as a catalyst and a high hydrogen pressure. Among the various ligands described as useful in said complexes are several tertiary phosphines, including triphenyl phosphine.

It is an object of the present invention to provide a homogeneous process for the preparation of hydrogenated derivatives of certain compounds containing an activated carbonyl group.

SUMMARY OF THE INVENTION

In accordance with the present invention, it has been found that hydrogenated derivatives of compounds having one of the following formulas $RH_2C-CO-CH_2R$ $CH_3-CO-\underset{R}{\underset{|}{\bigcirc}}$ $RH_2C-CO-\bigcirc$ wherein R is —Cl, —Br, —F or —OH, can be prepared in a homogeneous process by contacting a solution of the compound with hydrogen in the presence of a catalyst comprising a ruthenium triphenyl phosphine complex and a strong acid.

DESCRIPTION OF THE PREFERRED EMBODIMENTS

As mentioned above, in accordance with the present invention it has been discovered that certain compounds containing an activatable carbonyl group may be converted to their hydrogenated derivatives in a homogeneous process if the reaction is carried out in the presence of a specific ruthenium catalyst. In this regard it should be noted that the key to the present invention is the selection of a particular catalyst for the substrate being hydrogenated. Thus, it has been found that for substrates having one of the above-mentioned formulas, it is essential that the catalyst employed be a ruthenium triphenyl phosphine complex. As was also mentioned above, it has also been found in accordance with the present invention that improved results are achieved if the catalyst contains, in addition to the ruthenium triphenyl phosphine, a strong acid. The substrates, catalysts, solvents and reaction conditions which may be employed in carrying out the present invention are described in detail below.

SUBSTRATE

As was mentioned above, the substrates which may be hydrogenated in accordance with the present invention are compounds having one of the following formulas $RH_2C-CO-CH_2R$ $CH_3-CO-\underset{R}{\underset{|}{\bigcirc}}$ $RH_2C-CO-\bigcirc$ wherein R is —Cl, —Br, —F or —OH.

All of these substrates, which are derivatives of acetone or acetophenone, are either commercially available or can be prepared quite readily by anyone skilled in the art.

Representative compounds which may be employed include
1,3 dihydroxy acetone, 1,3 dichloro acetone,
1,3 dibromo acetone,
1,3 difluono acetone,
-hydroxyacetophenone,
o-chloroacetophenone,
o-bromoacetophenone
o-fluoroacetophenone,
α-hydroxyacetophenone,
α-chloroacetophenone,
α-bromoacetophenone, and
α-fluoroacetophenone.

In connection with the acetophenone derivatives, these materials may also have other substituents attached to the phenyl group thereof, provided that the other substituents do not interfere with the hydrogenation reaction.

CATALYST

As was mentioned above, the catalyst employed in the process of the present invention comprises
a. a ruthenium triphenyl phosphine, and
b. a strong acid.

The active form of the ruthenium triphenyl phosphine compounds which may be utilized in accordance with the present invention is represented by the following formula:

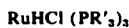

RuHCl (PR'₃)₃ wherein R' is phenyl or a substituted phenyl selected from the group consisting of para-methyl phenyl and para-methoxy phenyl. In accordance with the present invention it has been found that ligands other than those mentioned above, including other tertiary phosphines, do not produce satisfactory results when employed in a homogeneous process for hydrogenating the substrates employed herein.

The active form of the ruthenium triphenyl phosphine may be introduced into the hydrogenation reaction mixture by any one of the following three methods.

First, the active form may be prepared, isolated, and introduced directly into the reaction medium. If this procedure is utilized the material is prepared in a two-step process in accordance with the following reactions:

(a)
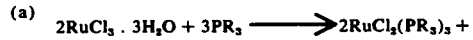

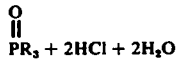
PR₃ + 2HCl + 2H₂O (b)

Reaction (a) may be carried out by the procedure described in Stephenson et al., *J. Inorg. Nuclear Chem.*, 1966, Vol. 28, page 945. Reaction (b) may be carried out by the procedure described in Hallman et al., *J. Chem. Soc.* (A), 1968, page 1343.

Alternatively, the active form may be prepared in situ in the reaction medium either by adding the dichloro derivative, prepared as in reaction (a) above, to the reaction mixture or by adding the starting materials as employed in reaction (a) above to said mixture. Preferred results are achieved when the starting materials — i.e., the ruthenium chloride and the triphenyl phosphine — are added to the reaction mixture and the active catalyst is formed in situ. When this procedure is employed, it has been found that the molar ratio of triphenyl phosphine to ruthenium chloride is preferably equal to at least 2 to 1. At ratios below this amount, the rate of the hydrogenation reaction is considerably slower and, although the reaction rate does increase somewhat as this ratio is increased, the further increase does not justify the larger amounts of triphenyl phosphine required.

In addition to the specific ruthenium triphenyl phosphine described above, the catalysts useful in the process of the present invention also include a strong acid. It has been found that the inclusion of a small amount of such an acid results in an unexpected increase in the rate of the hydrogenation reaction. As used herein, the term strong acid refers to acids which have a $pK_a$ value equal to less than about 1.

Representative acids which may be employed in the catalyst useful in the present invention include, for example, hydrochloric acid; sulfuric acid; sulfonic acids such as toluene sulfonic acids; trifluoromethyl sulfonic acid ($CF_3SO_3H$) and fluoboric acid ($HBF_4$). Of these it is preferred to employ hydrochloric acid. In this regard it should be noted that when the ruthenium triphenyl phosphine component of the catalyst is prepared in situ by either of the previously described methods 1 mol of hydrochloric acid is generated for each mol of the triphenyl phosphine prepared. Thus it is possible to prepare in situ both components of the catalyst system utilized herein.

PROCESS

In carrying out the present invention the substrate is dissolved in a suitable solvent and the catalyst is added thereto. Hydrogen is then introduced into the reaction mixture until the substrate has been hydrogenated to the extent desired.

Any solvent which is chemically inert and which does not interfere with the hydrogenation reaction may be employed. However, it is emphasized that the particular solvent employed must be one in which both the substrate and the catalyst are soluble either at room temperature or at the temperature at which the reaction is carried out. One solvent system which has been found to be particularly useful is a mixture of a protoropic, organic polar solvent and water. The amount of solvent employed has not been found to be narrowly critical to the present invention and any amount of solvent which will dissolve the substrate and catalyst may be employed. As used herein, the term polar solvents includes those which have a dielectric constant equal to at least about 20. Representative solvents which may be utilized include, for example, methanol, ethanol, methyl cellosolve and acetic acid. However, it is critical that such a solvent be prototropic — i.e., have an active hydrogen available. When this type of solvent is employed, it is preferred to also include, as part of the solvent system, an amount of water equal to from about 1 percent to about 30 percent by weight based on the total weight of said system. As will be apparent to those skilled in the art, the water need not be added as such and may be included in one of the other materials added to the reaction mixture.

A further improvement in the process of the present invention has been achieved by including a weakly basic solvent in the above-mentioned system and, while it is not essential to the present invention, there is preferably included in the reaction mixture an amount of such a solvent. The advantage of including such a material in the reaction mixture is to increase the solubility of the ruthenium triphenyl phosphine. As used herein, the term weakly basic solvent refers to materials having a $K_b$ value equal to less than about $1 \times 10^{-13}$ — i.e., a $pK_b$ equal to less than about 13. Representative weakly basic solvents which may be employed include, for example, dimethylformamide, N-methylpyrrolidone, dimethylacetamide and diethylacetamide. When a weakly basic solvent is utilized it should be employed in an amount equal to at least one mol for each mol of strong acid in the reaction mixture.

Instead of the mixed solvent system discussed above, it has also been found that a weakly basic solvent, as previously described, can be employed as the only solvent in the reaction mixture. The use of such a solvent is preferred for hydrogenating the acetophenone derivatives that may be employed in the process of this invention.

The substrate concentration has not been found to be critical to the process of the present invention. However, as this concentration decreases the rate of the reaction generally increases.

Concerning the catalyst concentration, this also has not been found to be narrowly critical to the process of the present invention. Thus, any amount of catalyst which is both soluble in the reaction mixture and which is sufficient to accelerate the reaction may be employed. Preferred results have been achieved with catalyst concentrations equal to from about 0.25 gram to about 0.5 gram per 40 grams of substrate being hydrogenated.

When either alpha-chloro or alpha-bromo acetophenone is employed as the substrate, it is preferred to include in the reaction mixture an additional amount of the triphenyl phosphine ($PR_3$) to prevent inactivation of the catalyst by what is believed to be an oxidative addition reaction between this type of substrate and the active form of the catalyst. The amount of triphenyl phosphine added for this purpose is preferably equal to at least 10 mols per mol of active catalyst and this excess may be added either at the beginning of the reaction or periodically during the course of the reaction. Although some product will be produced even if this additional amount is not added, the yield will be low and it is, therefore, preferred to include the additional amount.

The hydrogenation process of the present invention is carried out utilizing techniques and apparatus which are well known to those skilled in the art except as otherwise noted herein.

The reaction temperature employed in the hydrogenation process may be varied over a wide range. However, preferred results are achieved at temperatures in the range of from about 75° C. to about 150° C. It has been found that at temperatures below about 75° C. the rate of reaction is slow and, therefore, may not be practical. It should also be noted that, in some instances, depending upon the substrate being hydrogenated, the catalyst and the solvent employed, it may be necessary to employ heat to achieve a complete solution of the substrate and catalyst in the solvent. However, it has also been found that at temperatures above about 150° C. no further increase in the reaction rate is noted and it is, therefore, not preferred to carry out the reaction at temperatures much above 150° C. Also, at temperatures above about 150° C. the catalyst may not be stable and, due to decarbonylation of the substrate, carbonyl complexes of the ruthenium triphenyl phosphine may occur. These complexes are not efficient catalysts for the hydrogenation reaction.

Hydrogenation is preferably introduced into the reaction mixture continuously during the course of the reaction and the reaction may be carried out under any positive hydrogen pressure. However, preferred results are achieved at hydrogen pressures of from about 20 to about 60 psi. Above about 50 psi, the reaction is pressure independent — i.e., there is no further increase in the reaction rate as the pressure is increased — and it is, therefore, not desirable to operate at a much higher pressure. Also, at lower pressures the reaction times are longer than would be desirable in a commercial operation.

The reaction time depends upon the substrate, catalyst, pressure, and temperature employed. Generally, the reaction will be completed in reaction times of about 0.1 to about 5 hours.

The process of this invention may conveniently be carried out in any suitable type of apparatus which enables intimate contact with the reactants and control of the operating conditions. For example, the process of the present invention may suitably be carried out by passing, concurrently, the solutions of substrate and catalyst upward through a vertical reactor and simultaneously passing a supply of hydrogen gas under pressure upward through the reactor. The process may be carried out in batch, semi-continous or continuous operation and is preferably carried out in a continuous operation using a plurality of reactors arranged in a series.

The hydrogenated compounds prepared by the process of the present invention have one of the following structures:

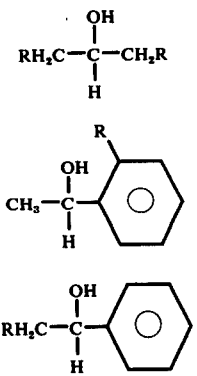

wherein R is —Cl, —Br, —F or —OH.

In accordance with the present invention, dihydroxy acetone is converted to glycerol which is useful in a variety of applications including, for example, as a plasticizer for regenerated cellulose, for sweetening and preserving foodstuffs, as a humectant, hydraulic fluid and antifreeze. The halogenated acetone derivatives are useful as flame retardant polyols in the preparation of polyesters (*Chem. Abstracts*, Vol. 66, 11408c) and, when converted to a phosphate, as textile fireproofing agents (*Chem. Abstracts*, Vol. 62, 33143p). The dichloroacetone derivative is known to be useful as a fiber retention additive in paper making processes (*Chem. Abstracts*, Vol. 67, 65085j) and the difluoroacetone derivative has been reported as a selective rodenticide (*Chem. Abstracts*, Vol. 63, 12259a).

The substituted acetophenone can be quite readily converted to the corresponding substituted styrene derivatives which are useful as monomers in the preparation of a variety of polymeric materials including both homopolymers and copolymers with other monomers. The o-fluoroacetophenone derivative has been reported as exhibiting choleretic activity (*J. Organic Chemistry*, Vol. 27, p. 2669–70, 1962). The alpha-hydroxyacetophenone derivative is useful as an antifogger and sensitizer for silver halide emulsions (*Chem. Abstracts*, Vol. 73, 82505n).

In order to describe the present invention so that it may be more clearly understood, the following examples are set forth. These examples are set forth primarily for the purpose of illustration and any enumeration of detail contained therein should not be interpreted as a limitation on the concept of the present invention.

In the examples, low pressure hydrogenations — i.e., those at pressures up to about 60 psi hydrogen, were performed by the pop bottle technique described in Shriver, *Manipulation of Air Sensitive Compounds*, McGraw Hill, 1969, pages 156–158. Hydrogenations at higher pressures were carried out in a 300 ml stainless steel autoclave equipped with a temperature controller and temperature and pressure recorders. Samples were removed periodically during the course of the reaction, acetylated and analyzed by gas-liquid chromatography. When given, the amount of desired product in the sample is expressed in terms of percent by weight based upon the total weight of unreacted starting material and product in the sample.

The half life period ($t_{1/2}$) refers to the time, in minutes, required for one half of the substrate to react to form the hydrogenated derivative thereof.

EXAMPLE 1

Preparation of ruthenium chloride triphenyl phosphine ($RuCl_2(P\phi_3)_3$)

Into a 200 ml pop bottle — i.e., a cappable, glass, pressure bottle, there was added a solution of 0.4 gram of ruthenium trichloride trihydrate dissolved in 50 ml of methanol and 2.4 grams of triphenyl phosphine. The bottle was evacuated and the reaction mixture stirred for 3 hours at 70° C. At the end of this time, the reaction mixture was cooled to room temperature, the brown crystals were removed by filtration and were washed with methanol. There resulted 1.5 grams of product identified as ruthenium chloride triphenyl phosphine. Analysis of the product indicated 9.3 percent phosphorus and 67.75 percent carbon. These compare favorably with the theoretical values of 9.7 percent phosphorus and 67.76 percent carbon.

EXAMPLE 2

Preparation of ruthenium hydridochloride triphenyl phosphine ($RuHCl(P\phi_3)_3$)

A solution was prepared comprising:
1.5 grams of ruthenium chloride triphenyl phosphine,
150 ml of degassed benzene, and
0.22 ml of triethylamine to take up HCl generated during the reaction.

Hydrogen was bubbled through the solution for 15 hours at the end of which time the solution was filtered and the solvet evaporated until crstallization occurred. The crystals were filtered, washed with ether and dried.

EXAMPLE 3

Into a 200 ml pop bottle there were added:
1 gram of 1,3 dihydroxy acetone,
10 ml of N-methyl-pyrrolidone,
15 ml of methyl cellosolve, and
2 ml of water.

The bottle was capped, evacuated to remove oxygen and a slight positive pressure of hydrogen introduced. The resulting solution was heated to 75° C. and, to the solution there was added 0.25 grams of ruthenium chloride triphenyl phosphine prepared as described in Example 1, dissolved in 5 ml of N-methyl pyrrolidone. The hydrogen pressure was increased to 50 psi and the temperatures of the reaction mixture maintained at 75° C. Samples of the reaction mixture were removed periodically during the course of the reaction and analyzed by gas-liquid chromatography. At the end of 18 minutes, ½ of the dihydroxy acetone had reacted — i.e., $t_{1/2}$ was equal to 18 minutes.

EXAMPLE 4

Into a 200 ml pop bottle there were added:
1.4 grams of 1,3 dichloroacetone,
10 ml of N-methyl-pyrrolidone,
15 ml of methyl cellosolve, and
2 ml of water.

The bottle was capped, evacuated to remove oxygen and a slight positive pressure of hydrogen introduced. The resulting solution was heated to 75° C. and, to the solution there was added 0.25 grams of ruthenium chloride triphenyl phosphine prepared as described in Example 1, dissolved in 5 ml of N-methyl pyrrolidone. The hydrogen pressure was increased to 50 psi and the temperature of the reaction mixture maintained at 75° C. Samples of the reaction mixture were removed periodically during the course of the reaction and analyzed by gas-liquid chromatography. At the end of 10 minutes, ½ of the dichloroacetone had reacted — i.e., $t_{1/2}$ was equal to 10 minutes.

EXAMPLE 5

Into a 17 ml pop tube there was added 0.15 gram of ruthenium chloride triphenyl phosphine. The tube was capped, evacuated to remove oxygen and 5 ml of dimethylacetamide was added. A slight positive pressure of hydrogen was introduced and the brown slurry turned to a deep red solution within 5 minutes. At this time, 0.5 ml of ortho-chloroacetophenone was introduced. The hydrogen pressure was increased to 30 psi and the tube placed in an oil bath at 100° C. Samples of the reaction mixture were removed periodically during the course of the reaction and analyzed by gas-liquid chromatography. After 3½ hours, a sample contained 38 percent of the alcohol derivative. A second sample removed after 5 hours contained 52 percent by weight of 1-(2-chlorophenyl)ethanol

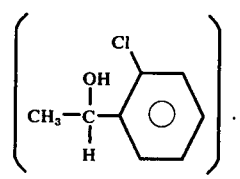

EXAMPLE 6

Into a 200 ml pop bottle there was added 0.3 gram of ruthenium chloride triphenyl phosphine prepared as described in Example 1. The bottle was capped, evacuated to remove oxygen and 20 ml of diethylacetamide was added. Hydrogen was introduced to a pressure of 20 psi and, after 5 minutes, 2 ml of ortho-chloroacetophenone were added. The pop bottle was then placed in an oil bath at 118° C. At the end of 3 hours a sample was removed and analyzed by gas-liquid chromatography. Analysis indicated that the sample contained 91 percent by weight 1-(2-chlorophenyl) ethanol.

EXAMPLE 7

Into a 17 ml pop tube, there was added 0.25 gram of ruthenium chloride triphenyl phosphine prepared as described in Example 1. The bottle was capped, evacuated to remove oxygen and 6 ml of dimethylacetamide was added. Hydrogen was then introduced to a pressure of 20 psi and, when the color had turned red, 1 gram of alpha-chloromethylacetophenone dissolved in 5 ml of dimethylacetamide was introduced. The tube was then placed in an oil bath at 75° C. At the end of 45 minutes, the color of the reaction mixture had changed to brown and 0.6 gram of triphenyl phosphine were added resulting in the color changing to red again. The tube was then placed in an oil bath at 85° C. and maintained at that temperature for 4 hours resulting in the production of 2-chloro-1-phenyl ethanol

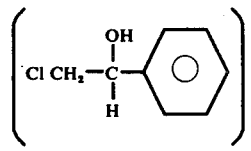

What is claimed is:

1. A homogeneous hydrogenation process comprising contacting a solution of a substrate having one of the following formulas

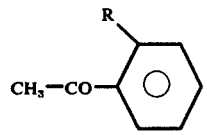

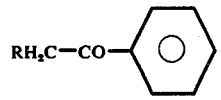

wherein R is —Cl, —Br, —F or —OH, with hydrogen under positive pressure in the presence of a catalyst comprising a ruthenium triphenyl phosphine complex having the following general formula:

wherein R' is phenyl, p-methyl phenyl, or p-methoxy phenyl and a strong acid having a pKa equal to less than about 1.

2. A process, as claimed in claim 1, wherein the substrate is dissolved in dimethylacetamide.

3. A process, as claimed in claim 1, wherein the ruthenium triphenyl phosphine complex and strong acid are prepared in situ.

4. A process, as claimed in claim 3, wherein the ruthenium triphenyl phosphine complex is prepared from $RuCl_2(PR'_3)_3$ wherein R' is phenyl, p-methyl phenyl or p-methoxy phenyl.

5. A process, as claimed in claim 3, wherein the ruthenium triphenyl phosphine complex is prepared from $RuCl_3$ and $PR'_3$ wherein R' is phenyl, p-methyl phenyl or p-methoxy phenyl.

6. A process, as claimed in claim 1, wherein R' is phenyl.

7. A process, as claimed in claim 1, wherein the strong acid is hydrochloric acid.

8. A process, as claimed in claim 1, wherein the reaction is carried out in a mixed solvent system comprising
   a. a prototropic organic polar solvent,
   b. a weakly basic solvent having a $pK_b$ equal to less than about 13 in an amount equal to at least 1 mol per mol of strong acid in the reaction system, and
   c. water.

9. A process, as claimed in claim 8, wherein the solvent system comprises
   a. methyl cellosolve,
   b. N-methyl pyrrolidone, and
   c. water.

10. A process, as claimed in claim 9, wherein the solvents are utilized in a volumetric ratio of a:b:c of 15:10:2.

11. A process, as claimed in claim 1, wherein the reaction is carried out at a temperature in the range of from about 75° C. to about 150° C.

12. A process, as claimed in claim 1, wherein the reaction is carried out at a pressure of from about 20 psi to about 60 psi.

13. A process, as claimed in claim 1, wherein the substrate is 1,3-dichloroacetone.

14. A process, as claimed in claim 1, wherein the substrate is 1,3-dihydroxyacetone.

15. A process, as claimed in claim 1, wherein the substrate is o-chloroacetophenone.

16. A process, as claimed in claim 1, wherein the substrate is alpha-chloroacetophenone.

17. A process, as claimed in claim 1, wherein the substrate has the following formula

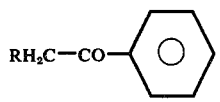

wherein R is —Cl or —Br, and there is also included in the reaction mixture a triphenyl phosphine having the formula PR' wherein R' is phenyl, p-methyl phenyl or p-methoxy phenol in an amount equal to at least 10 mols per mol of ruthenium triphenyl phosphine complex.

* * * * *

UNITED STATES PATENT AND TRADEMARK OFFICE
CERTIFICATE OF CORRECTION

PATENT NO. : 4,024,193
DATED : May 17, 1977
INVENTOR(S) : Walter M. Kruse

It is certified that error appears in the above-identified patent and that said Letters Patent are hereby corrected as shown below:

Column 3, line 4, "-hydroxyacetophenone," should read
-- 0-hydroxyacetophenone, --.
Column 6, line 63, "Vol. 62," should read -- Vol. 72, --.

Signed and Sealed this

Tenth Day of April 1979

[SEAL]

Attest:

RUTH C. MASON
Attesting Officer

DONALD W. BANNER
Commissioner of Patents and Trademarks